(12) United States Patent
Jang et al.

(10) Patent No.: US 6,514,293 B1
(45) Date of Patent: Feb. 4, 2003

(54) PROSTHETIC FOOT

(75) Inventors: Tae Seong Jang, Taejon (KR); Dong Hee Lee, Taejon (KR); Jung Ju Lee, Taejon (KR); Yong San Yoon, Taejon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 09/693,943

(22) Filed: Oct. 23, 2000

(30) Foreign Application Priority Data

Apr. 3, 2000 (KR) .......................... 2000-17337

(51) Int. Cl.⁷ ................................. A61F 2/66
(52) U.S. Cl. ........................... 623/55; 623/52
(58) Field of Search ................ 623/49, 50, 52, 623/55

(56) References Cited

U.S. PATENT DOCUMENTS

| 5,037,444 | A |   | 8/1991  | Phillips         |        |
|-----------|---|---|---------|------------------|--------|
| 5,062,859 | A | * | 11/1991 | Naeder           | 623/55 |
| 5,116,385 | A |   | 5/1992  | Allard et al.    |        |
| 5,156,632 | A | * | 10/1992 | Wellershaus      | 623/55 |
| 5,158,570 | A |   | 10/1992 | Schey et al.     |        |
| 5,181,932 | A |   | 1/1993  | Phillips         |        |
| 5,219,365 | A |   | 6/1993  | Sabolich         |        |
| 5,258,038 | A |   | 11/1993 | Robinson et al.  |        |
| 5,258,039 | A |   | 11/1993 | Goh et al.       |        |
| 5,443,527 | A |   | 8/1995  | Wilson           |        |
| 5,443,528 | A |   | 8/1995  | Allen            |        |
| 5,486,209 | A |   | 1/1996  | Phillips         |        |
| 5,509,937 | A |   | 4/1996  | Allard et al.    |        |
| 5,571,213 | A |   | 11/1996 | Allen            |        |
| 5,593,457 | A |   | 1/1997  | Phillips         |        |
| 5,653,767 | A |   | 8/1997  | Allen et al.     |        |
| 5,695,526 | A |   | 12/1997 | Wilson           |        |
| 5,695,527 | A |   | 12/1997 | Allen            |        |
| 6,197,066 | B1 | * | 3/2001 | Gabourie         | 623/52 |

* cited by examiner

Primary Examiner—Bruce Snow
(74) Attorney, Agent, or Firm—Duane Morris LLP

(57) ABSTRACT

Disclosed herewith is a prosthetic foot. The prosthetic foot is to be connected to a pylon that is utilized for the substitution of the shinbone of an amputee. The prosthetic foot includes an ankle portion to be secured to the pylon. A plurality of curved portions are extended from one end of the ankle portion. A sole portion is extended from one end of the curved portions. The ankle portion, the curved portions and the sole portion form a single integrated plate spring structure.

13 Claims, 6 Drawing Sheets

PROSTHETIC FOOT

BACKGROUND OF THE INVENTION

1. Field of the Invention

The present invention relates generally to prosthetic feet utilized to allow below-knee amputees to walk, and particularly to a prosthetic foot that is capable of generating a suitable thrust for propelling the deficient limb of an amputee forward in walking.

2. Description of the Prior Art

A below-knee amputee cannot be provided with a thrust that can be obtained by pushing the ground with his toes, owing to the loss of plantar flexors. It is reported that he consumes 20% more oxygen than an able-bodied person, when the below-knee amputee walks at a speed of 50 to 90 m/min. This means that the below-knee amputee consumes more energy than an able-bodied person in walking, so that he gets easily exhausted.

In order to reduce the above-mentioned below-knee amputees' difficulty, there has been developed improved prosthetic feet that allow the below-knee amputees to walk naturally and with low energy consumption.

FIG. 1 is a schematic diagram showing a conventional energy storage type prosthetic foot.

The conventional prosthetic foot shown in FIG. 1 is disclosed by Korean Pat. No. 0155591 entitled "energy storage type prosthetic foot pylon".

Referring to the drawings of the Patent, the conventional prosthetic foot pylon comprises a first pylon member 18, a second pylon member 20, one or more plate springs 22 combined with the first and second pylon members 18 and 20 for controlling the axial and rotational movements of the first and second pylon members 18 and 20, and a foot member 14 fixed to the second pylon member 20.

The conventional prosthetic foot pylon is characterized in that each plate spring 22 is combined with the first and second pylon members 18 and 20. Consequently, forces applied to the pylon members 18 and 20 are stored in the plate spring 22 as elastic energy, and upon the removal of the forces, the energy stored in the plate spring 22 is released to generate a thrust.

U.S. Pat. Nos. 5,181,932, 5,486,209 and 5,593,457 entitled "foot prosthetic having auxiliary ankle construction" and U.S. Pat. No. 5,037,444 entitled "prosthetic foot" disclose typical prosthetic feet and employ keels having plate spring structures.

U.S. Pat. No. 5,158,570 entitled "foot prosthesis having auxiliary ankle construction" and U.S. Pat. No. 5,258,038 entitled "prosthetic foot with ankle joint and toe member" disclose prosthetic feet in each of which a forefoot member, an ankle member and a heel member formed of thermoplastic material or composite material are connected to one another through joints. These are multi-piece prosthetic feet in which pivotable movement is performed while being resisted by elastomeric pads.

U.S. Pat. No. 5,219,365 entitled "prosthetic foot" discloses a prosthetic foot in which a forefoot member, an ankle member and a heel member are fabricated to be a single integrated keel and are formed of hardened acetal copolymers. A vertical through hole is formed in the keel and serves to connect the keel with leg assemblies. The arched configuration of the prosthetic foot increases the strength and dynamic characteristics of the foot.

U.S. Pat. No. 5,443,527 entitled "prosthetic foot and three-way ankle joint" and U.S. Pat. No. 5,695,526 entitled "one-piece mechanically differentiated prosthetic foot and associated ankle joint with syme modification" disclose prosthetic feet each of which includes an integrated instep and sole portion and is provided with joints to provide for three-axis rotation, dorsiflexion and planarflexion.

U.S. Pat. No. 5,443,528 entitled "coil spring prosthetic foot", U.S. Pat. No. 5,695,527 entitled "coil prosthetic foot", U.S. Pat. No. 5,653,767 entitled "prosthetic foot" and U.S. Pat. No. 5,571,213 entitled "prosthetic foot" disclose prosthetic feet that are fabricated of continuous springs. Each prosthetic foot comprises a foot center coil section, a heel extension section and a forefoot extension section that are formed of epoxy-like polymer associated with graphite fiber, a mixture of graphite fiber and glass fiber, Kevlar, spectra or one of other fiber materials. The prosthetic foot allows lateral medial torsional movement. The heel extension section integrated with the forefoot extension section is utilized, so that the prosthetic foot is designed to transmit energy from a heel to a forefoot effectively.

U.S. Pat. No. 5,258,039 entitled "energy storing composite prosthetic foot" discloses a keel that is λ-shaped, χ-shaped and σ-shaped. The keel is formed of resin impregnated carbon woven fabric composite material.

U.S. Pat. No. 5,509,937 entitled "prosthetic foot with enhanced heel control" and U.S. Pat. No. 5,116,385 entitled "medio-lateral control enhancing, cantilever-spring type prosthetic foot" disclose prosthetic feet each of which comprises a main forefoot leg, a rear leg and an intermediate leg connecting the forefoot leg with the rear leg and is S-shaped. In the prosthetic feet, cantilever spring members absorb energy from the heel portions when the heels are brought into contact with the ground. The prosthetic feet provide medio-lateral control and release energy during a toe-off stage.

As described above, a variety of prosthetic feet have been developed throughout the world. These prosthetic feet employ various-shaped keels, respectively.

However, some of the prosthetic feet include both leg portions and foot portions, so that pylons cannot be attached to the prosthetic feet and the prosthetic feet have complicated structures due to a large number of parts.

Additionally, the prosthetic feet have narrow allowable ranges of variation that cannot allow the prosthetic feet to be designed to correspond to individual amputee's physical conditions.

Accordingly, it is desired to develop a prosthetic foot that has adjustable design factors for amputee's individual physical conditions and is capable of being easily fabricated.

SUMMARY OF THE INVENTION

Accordingly, the present invention has been made keeping in mind the above problems occurring in the prior art, and an object of the present invention is to provide a prosthetic foot, which allows a below-knee amputee to walk naturally, which reduces energy consumption in walking, and which is easily worn due to its simple structure.

In order to accomplish the above object, the present invention provides a prosthetic foot to be connected to a pylon that is utilized for the substitution of the shinbone of an amputee, comprising: an ankle portion to be secured to the pylon; a plurality of curved portions extended from one end of the ankle portion; and a sole portion extended from one end of the curved portions; wherein the ankle portion, the curved portions and the sole portion form a single integrated plate spring structure.

In accordance with one feature of the present invention, the curved portions are a first curved portion and a second curved portion, the first curved portion having a first predetermined radius of curvature and being extended from the inner end of the ankle portion, the second curved portion having a second predetermined radius of curvature and connecting the first curved portion with the sole portion.

In accordance with one feature of the present invention, the foot further comprises a planar portion, the planar portion having a first predetermined length and being interposed between the first and second curved portions.

In accordance with one feature of the present invention, the sole portion has a second predetermined length and is inclined at a predetermined slope.

In accordance with one feature of the present invention, the foot further comprises a toe portion, the toe portion having a third predetermined radius of curvature and being extended from the outer end of the sole portion.

In accordance with one feature of the present invention, the foot further comprises first, second and third connecting portions, the first connecting portion connecting the first curved portion with the planar portion, the second connecting portion connecting the heel portion with the sole portion, the third connecting portion connecting the sole portion with the toe portion, the first, second and third connecting portions respectively having predetermined fillet radii so as to reduce the concentration of stresses.

In accordance with one feature of the present invention, the foot further comprises an aluminum pad, the aluminum pad being fixed to a portion of the ankle portion that is brought into contact with the pylon.

In accordance with one feature of the present invention, the foot further comprises an elastic polymer pad, the elastic polymer pad being interposed between the ankle portion and the aluminum pad so as to increase the compliance of the ankle portion.

In accordance with one feature of the present invention, the ankle portion, the aluminum pad and the elastic polymer pad are provided with one or more through-holes so as to receive a bolt.

In accordance with one feature of the present invention, the ankle portion, the curved portions and the sole portion are made of fiber reinforced composite material.

In accordance with one feature of the present invention, the fiber reinforced composite material is formed by associating epoxy-like polymer with one of various chopped or continuous fibers, such as carbon fiber, Kevlar, graphite fiber and glass fiber.

In accordance with one feature of the present invention, the fiber reinforced composite material is formed of unidirectional prepreg or woven fabric prepreg.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
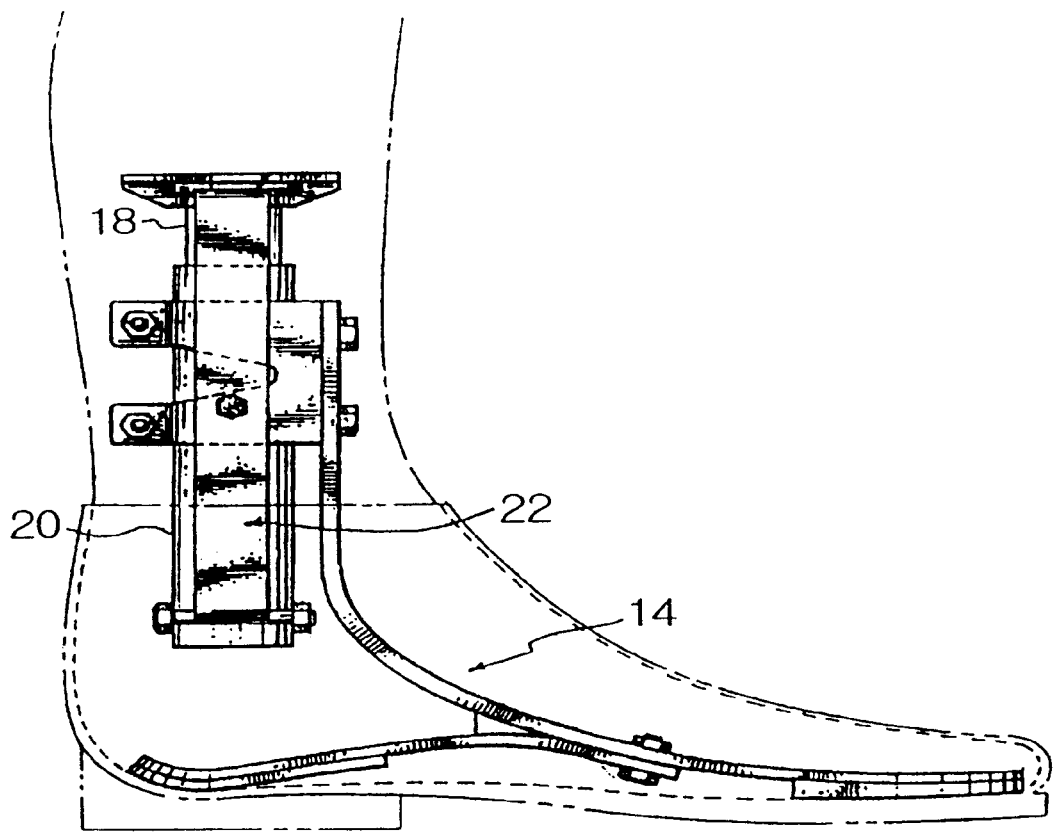
FIG. 1 is a schematic diagram showing a conventional energy storage type prosthetic foot.

Reference now should be made to the drawings, in which the same reference numerals are used throughout the different drawings to designate the same or similar components.

Hereinafter, an energy storage type prosthetic foot according to a preferred embodiment of the present invention will be described in detail, with reference to accompanying drawings.

Figure 2:
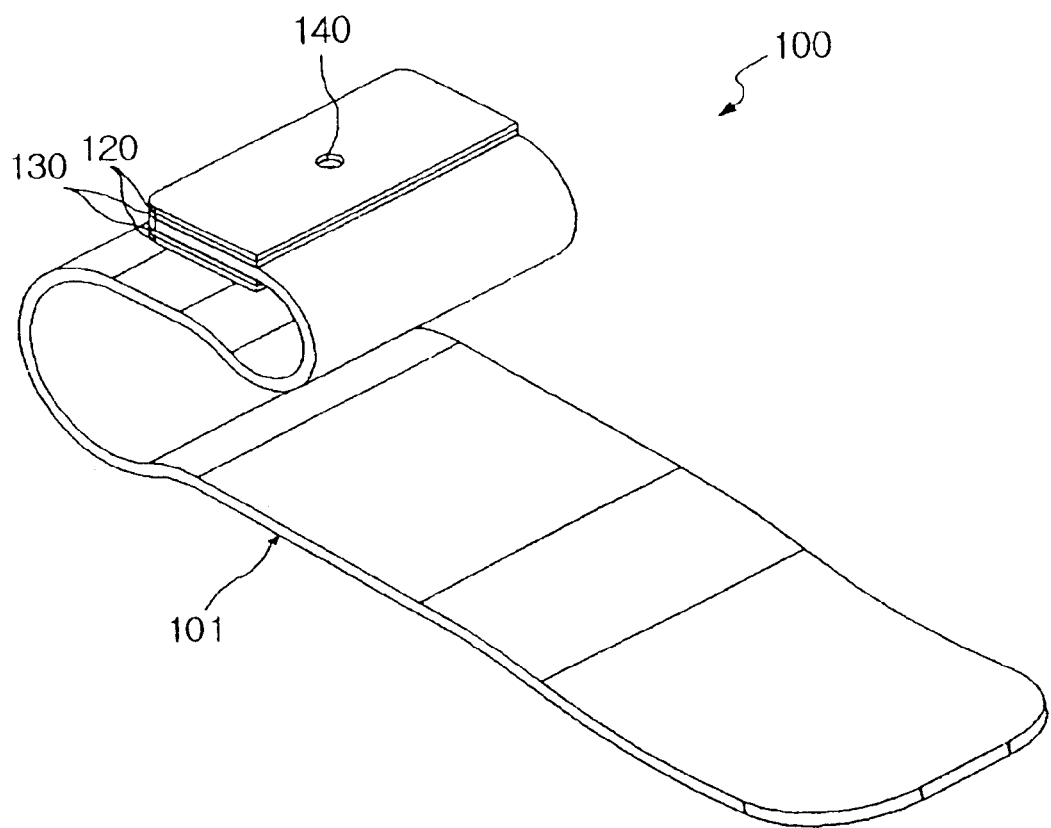
FIG. 2 is a perspective view showing the energy storage type prosthetic foot in accordance with the preferred embodiment of the present invention.
Figure 3:
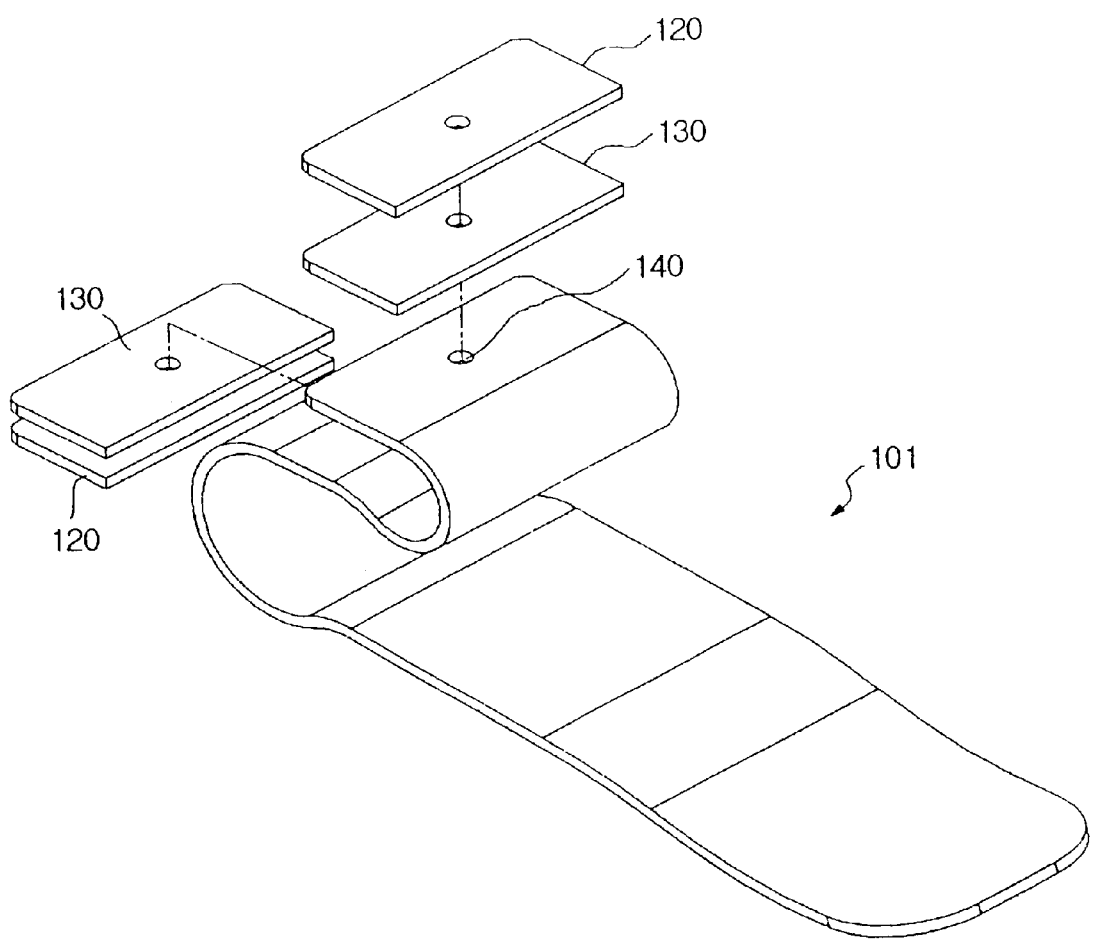
FIG. 3 is a perspective view showing the assembly of the prosthetic foot of FIG. 2.
Figure 4:
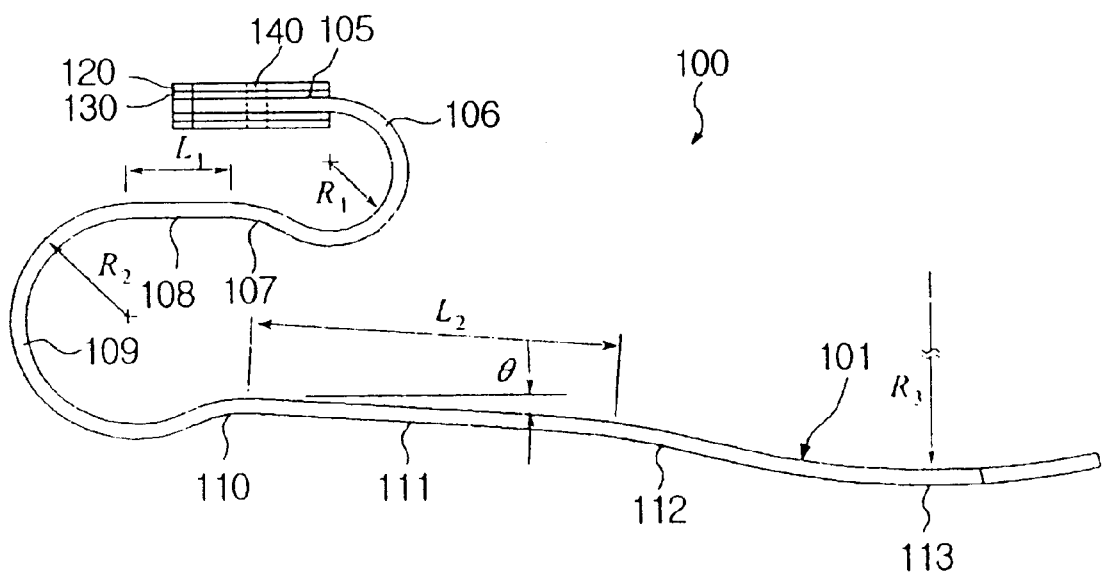
FIG. 4 is a side sectional view of the prosthetic foot of FIG. 2.
Figure 5:
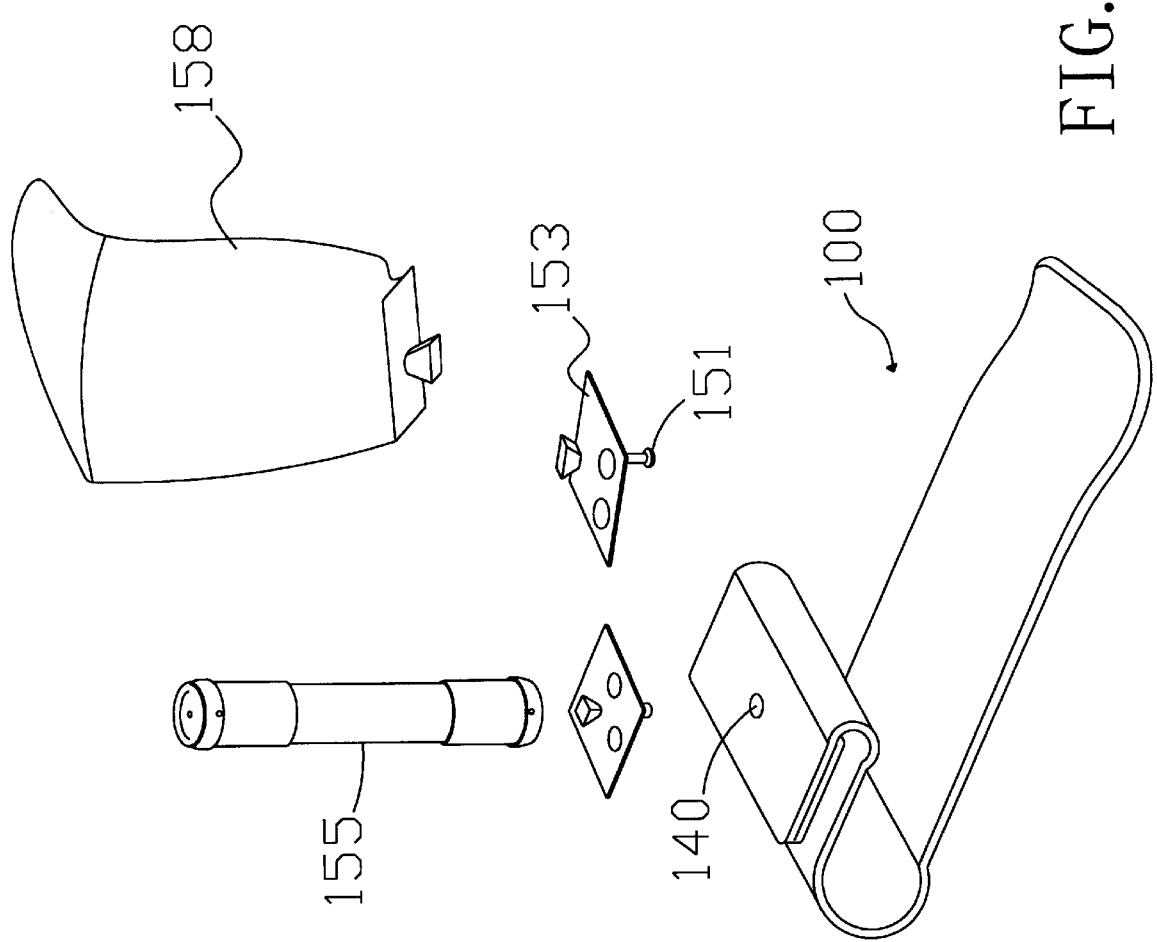
FIG. 5 is a perspective view showing the combination of the energy storage type prosthetic foot and a pylon.
Figure 6:
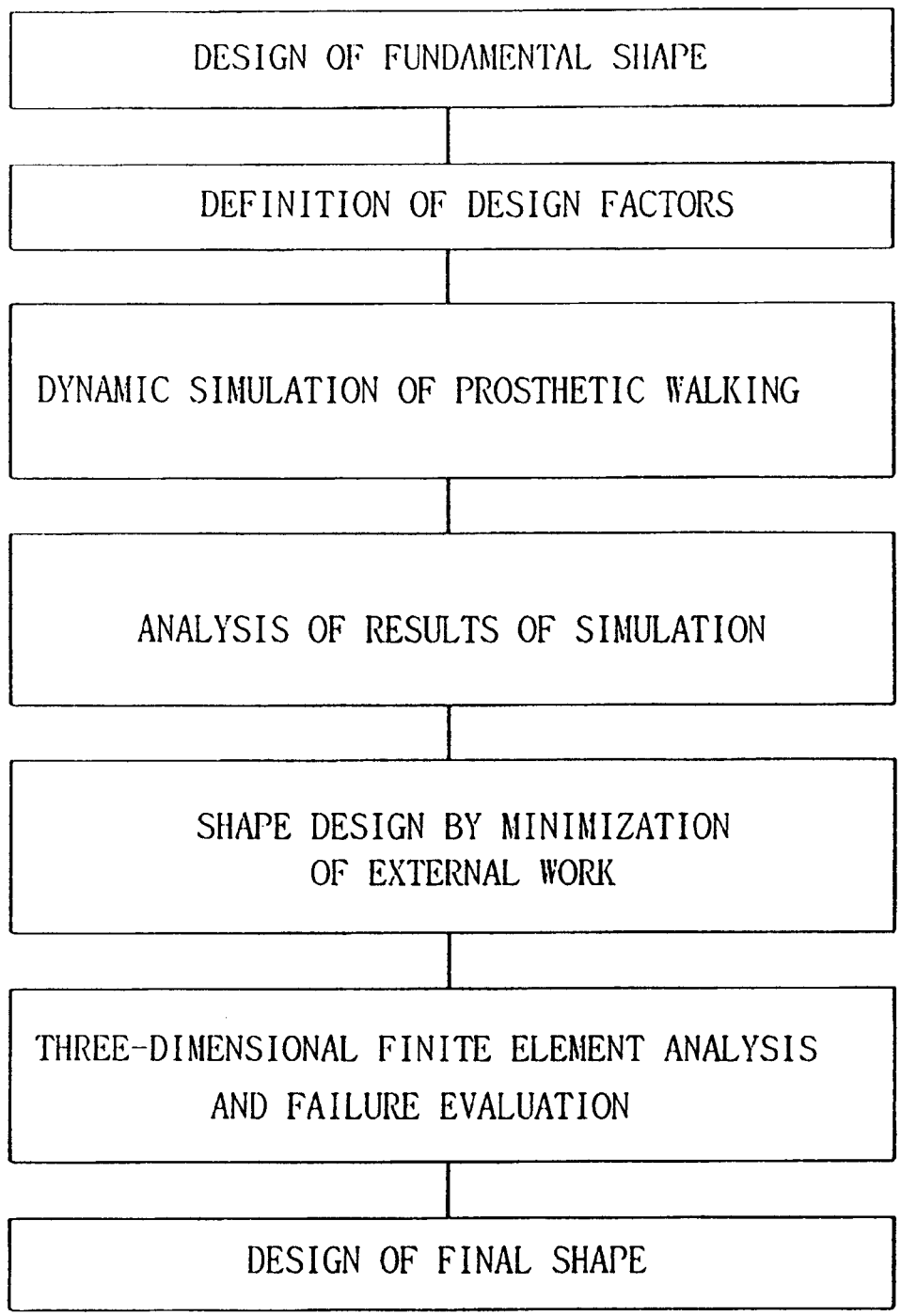
FIG. 6 is a flowchart showing the design procedure of the energy storage type prosthetic foot.

In the drawings, FIG. 2 is a perspective view showing the energy storage type prosthetic foot in accordance with the preferred embodiment of the present invention. FIG. 3 is a perspective view showing the assembly of the prosthetic foot of FIG. 2. FIG. 4 is a side sectional view of the prosthetic foot of FIG. 2. FIG. 5 is a perspective view showing the combination of the energy storage type prosthetic foot and a pylon. FIG. 6 is a flowchart showing the design procedure of the energy storage type prosthetic foot.

As shown FIGS. 2 to 5, the energy storage type prosthetic foot 100 comprises a keel 101 of composite material, a pair of aluminum pads 120 for connecting the keel 101 with a pylon 155, and a pair of elastic polymer pads 130 respectively interposed between the keel 101 and the aluminum pads 120. The two elastic polymer pads 130 are respectively positioned on the upper and lower surfaces of the ankle portion of the keel 101, and the two aluminum pads 120 are respectively positioned on the upper surface of one elastic polymer pad 130 and the lower surface of the other elastic polymer pad 130. Accordingly, the elastic polymer pads 130 are respectively positioned between the keel 101 and one of the aluminum pads 120.

The keel 101 includes an ankle portion 105, which constitutes one end of the keel 101 and is planar. A curved portion 106 having the radius of curvature R1 is extended from one end of the ankle portion 105. A planar portion 108 having a length L1 is extended from one end of the curved portion 106. A heel portion 109 having the radius of curvature R2 is extended from one end of the planar portion 108. A sole portion 111 having a length L2 and a slope $\theta$ is extended from one end of the heel portion 109. A toe portion 113 is extended from one end of the sole portion 111. When viewed from its side, the keel 101 is roughly S-shaped.

A through hole 140 is formed through the ankle portion 105 of the keel 101, the aluminum pads 120 and the composite polymer pads 130. An adaptor 153 is fixed to the ankle portion 105 of the keel 101 by means of a bolt 151 inserted into the through hole 140, and the pyramid-shaped projection of the adaptor 153 is connected to the pylon 155. Accordingly, the upper aluminum pad 120 is brought into contact with the adaptor 153, and the composite polymer pads 130 increase the compliance of the ankle portion 105 of the keel 101.

Such a keel 101 is preferably made of one of various fiber reinforced composite materials, such as epoxy-like polymer associated with one of various fibers, such as carbon fiber, Kevlar, graphite fiber and glass fiber. Chopped or continuous fiber may be employed as reinforcing fiber for the fiber reinforced composite material. Additionally, fiber reinforced laminated composite material formed of unidirectional prepreg or woven fabric prepreg may be employed as the material of the keel 101. Since the keel 101 has the planar portion 108 and the two curved portions, that is, the curved portion 106 and the heel portion 109, to form a plate spring structure, it is effectual that the keel 101 is made of fiber reinforced laminated material.

While the keel 101 is fabricated of fiber reinforced laminated composite material, the total thickness of the keel 101 can be varied by regulating the number of layers of laminated prepreg.

In particular, while the keel 101 is fabricated of unidirectional prepreg, it is effectual to utilize the lamination angle of quasi-isotropic composite material. For example, there may be employed the lamination patterns of 0°/60°/−60°/−60°/60°/0°/, 45°/−15°/−75°/−75°/−15°/45°, or −30°/30°/90°/90°/30°/−30°.

In order to regulate the bending rigidity of the keel 101 having a plate spring structure, the thickness of the keel 101 should be varied. In general, if the thickness of the keel 101 is increased, its rigidity is increased, whereas its flexibility is reduced. The optimum thickness of the keel 101 is determined in consideration of a wearer's weight, the wearer's range of activity, its flexibility characteristics, its energy storage characteristics and its structural stability.

Hereinafter, the energy storage of the prosthetic foot is described in detail.

The ankle portion 105 of the keel 101 is made planar to be connected to the adaptor 153, the adaptor 153 is fixed to the keel 101 by means of the bolt 151 inserted into the through hole 140, and the pyramid-shaped projection of the adaptor 153 is fixedly connected to the pylon 155. A curved portion 106 having the radius of curvature of R1, a planar portion 108 having a length of L1 and a heel portion 109 having the radius of curvature of R2 are extended from one end of the curved portion 106, so that a curved portion 106, a planar portion 108 and a heel portion 109 can store energy sufficiently. In particular, the length L1 of the planar portion 108 is concerned with the moment arm of load that is generated by weight exerted upon the ankle portion 105 of the keel 101 through the pylon 155, so that the length L1 affects the bending moment of the keel 101, the deformation amount of the keel 101 and the amount of elastic restoring energy of the keel 101. The size of the radius of curvature R1 of the curved portion 106 connecting the ankle portion 105 with the heel portion 109 determines the length of the keel 101 and affects the amount of stored energy and the transmission of impact. The size of the radius of curvature R2 of the heel portion 109 determines the length of the keel 101 and affects the amount of stored energy. The radii of curvature of the curved portion 106 and the heel portion 109 affects the flexibility of the keel 101.

A typical normal walk cycle consists of stance phase and swing phase. Stance phase comprises the period between foot strike and ipsilateral toe-off and lasts from bringing a heel into contact with the ground to removing toes from the ground. Swing phase follows stance phase. Stance phase is commonly divided into three periods: initial double limb support, single limb support and second double limb support. Initial double limb support is a period between foot strike and opposite toe-off, single limb support is a period between opposite toe-off and opposite foot strike and second double limb support is a period between opposite foot strike and toe-off.

The sole portion 111 has a slope θ and a length L2. The slope θ is an angle of the sole portion 111 with regard to a horizontal plane. The magnitude of the slope θ and the length L2 affect an equivalent spring constant on the sagittal plane of the keel 101 during the stance phase, thus affecting the energy storage capability of the keel 101. The toe portion 113 has a radius of curvature R3 and serves as a center of rotation of the below-knee portion of the leg. The toe portion 113 has sufficient length to effectively release elastic energy stored in the keel 101 by the repulsion of the ground during second double limb support.

A first connecting portion 107 connects the curved portion 106 with the planar portion 108, a second connecting portion 110 connects the heel portion 109 with the sole portion 111, and a third connecting portion 112 connects the sole portion 111 with the toe portion 113. The first, second and third connecting portions 107, 110 and 112 are curved-shaped respectively having fillet radii. These fillet radii are to prevent stresses from being concentrated on the portions 107, 110 and 112 due to abrupt changes in shape.

The width of the keel 101 may be varied to increase an amputee's convenience in walking. The number of the through holes 140 formed in the keel 101 can be adjusted, depending upon the structure of the adaptor 153 that is secured to the pylon 155.

As described above, the radii of curvature R1, R2 and R3, the lengths L1 and L2, and the slope θ are important design factors. The factors respectively have allowable ranges, so that they may be adjusted, depending upon individual physical conditions, such as the weight of an amputee and the range of activity of the amputee. The shape of the prosthetic foot may be varied to some extent, and the performance of the keel 101 may be varied by adjusting the design factors within the allowable ranges.

The connection of the keel to the pylon is described in detail.

As shown in FIG. 5, the adaptor 153 is inserted into the hole 140 that is formed through the ankle portion 105 of the keel 101, the aluminum pads 120 and the elastic polymer pads 130. The adaptor 153 is secured to the keel 101 by means of the bolt 151. The pyramid-shaped projection that is formed on the upper portion of the adaptor 153 is secured to the pylon 155. Accordingly, the adaptor 153 is interposed between the aluminum pad 120 and the pylon 155. Meanwhile, a knee socket 158 is connected to the pylon 155, with a pyramid-shaped projection formed on the lower portion of the socket 158 being secured to the pylon 155 in the same way as the pyramid-shaped projection formed on the upper portion of the adaptor 153 is secured to the pylon 155. As occasion demands, the through hole 140 that is formed in the aluminum pad 120 may be a simple hole, counter-bore, countersink or counter drill. Each elastic polymer pad 130 is disposed between the keel 101 and the aluminum pad 120 so as to increase the compliance of the ankle portion.

During walking, impact generated when the prosthetic foot is brought into contact with the ground is absorbed by the plate spring structure of the prosthetic foot, thus preventing excessive impact from being transmitted to an amputee's body. Bending moment generated in the keel 101 by the weight of a wearer and the repulsion of the ground causes the elastic deformation of the keel 101 during initial double limb support and single limb stance. At this time, elastic restoring deformation energy is stored in the plate spring structure of the keel 101. The elastic restoring deformation energy stored in the plate spring structure of the keel 101 is effectively released during toe-off stage, thereby generating a thrust for walking.

The design procedure of the energy storage type prosthetic foot is described in detail.

As shown in FIG. 6, first of all, the fundamental shape of the keel 101 is designed. Thereafter, design factors are defined depending upon individual amputee's physical conditions. In this case, the important design factors are the radii of curvature R1, R2 and R3 of the curved portion 106, the heel portion 109 and the toe portion 113, the lengths L1 and L2 of the planar portion 108 and the sole portion 111, and the slope θ of the sole portion 111.

After the design factors are defined, the dynamic simulation of prosthetic walking for the prosthetic foot is performed using an orthogonal array table. The results of the simulation are analyzed using an analysis of variance, and the shape of the prosthetic foot is designed in the basis of the analysis. At this time, the shape of the prosthetic foot is designed by minimizing the external work done by the knee when an amputee walks in the same way as a normal person walks.

In order to obtain the structural stability of the prosthetic foot, the final shape of the prosthetic foot is designed in consideration of the results of three-dimensional finite element analysis and failure evaluation.

The prosthetic foot suitable for individual amputee's physical conditions is fabricated through this procedure.

As described above, the keel of the energy storage type prosthetic foot is made of chopped or continuous fiber reinforced composite material, or fiber reinforced laminated composite material, so that the keel has a high specific rigidity, a high specific strength and a light weight.

The keel of the energy storage type prosthetic foot forms a single plate spring structure. Accordingly, the prosthetic foot absorbs impact when brought into contact with the ground, thereby preventing excessive impact from being transmitted to an amputee's body. Additionally, bending deformation generated in the keel by the weight of a wearer and the repulsion of the ground during initial double limb support and single limb support allows the recoverable strain energy to be stored in the plate spring structure of the keel, and the recoverable strain energy is effectively released during a toe-off stage, thereby generating a thrust for walking.

Furthermore, the energy storage type prosthetic foot provides the biomechanical functions of feet so as to reduce the energy consumed in prosthetic walking and to allow an amputee to perform various activities such as sport, thereby improving an amputee's rehabilitation and welfare.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A prosthetic foot to be connected to a pylon that is utilized for the substitution of the shinbone of an amputee, comprising:
   an ankle portion to be secured to the pylon;
   a sole portion;
   a plurality of curved portions connecting said ankle portion with said sole portion, including:
      a first curved portion having a first predetermined radius of curvature and extending from a forward facing end of said ankle portion;
      a second curved portion having a second predetermined radius of curvature and extending from a rearward facing end of said sole portion; and
   a planar portion having a first predetermined length and connecting the other ends of said first curved portion and said second curved portion;
   a first connecting portion connecting the first curved portion with said planar portion;
   a second connecting portion connecting a heel portion with said sole portion; and
   a third connecting portion connecting said sole portion with said toe portion,
   wherein said first, second and third connecting portions respectively having predetermined fillet radii so as to reduce the concentration of stresses, and
   wherein said ankle portion, said sole portion, said plurality of curved portions and said planar portion have substantially the same constant thickness.

2. The foot according to claim 1, wherein said sole portion has a second predetermined length and is inclined at a predetermined slope.

3. The foot according to claim 2, further comprising a toe portion, said toe portion having a third predetermined radius of curvature and extending from a forward facing end of said sole portion.

4. The foot according to claim 1, further comprising an aluminum pad, said aluminum pad being fixed to a portion of said ankle portion that is brought into contact with said pylon.

5. The foot according to claim 4, further comprising an elastic polymer pad, said elastic polymer pad being interposed between said ankle portion and said aluminum pad so as to increase the compliance of said ankle portion.

6. The foot according to claim 5, where said ankle portion, said aluminum pad and said elastic polymer pad are provided with a through hole so as to receive a bolt.

7. The foot according to claim 1, where said ankle portion, said curved portions and said sole portion are made of fiber reinforced composite material.

8. The foot according to claim 7, where said fiber reinforced composite material is formed by associating epoxy polymer with one of various chopped or continuous fibers, such as carbon fiber, Kevlar, graphite fiber and glass fiber.

9. The foot according to claim 7, where said fiber reinforced composite material is formed of unidirectional prepreg or woven fabric prepreg.

10. The foot according to claim 8, where said fiber reinforced composite material is formed of unidirectional prepreg or woven fabric prepreg.

11. A prosthetic foot to be connected to a pylon that is utilized for the substitution of the shinbone of an amputee, comprising:
    a first planar portion to be secured to the pylon;
    a second planar portion parallel to said first planar portion;
    a first curved portion having a first predetermined radius of curvature R1 connecting said first planar portion with said second planar portion;
    a sole portion; and
    a second curved portion having a second predetermined radius of curvature R2 connecting said second planar surface with said sole portion,
    wherein a distance between said first and second planar portions is less than twice R1,
    wherein said first and second planar portions, said sole portion, and said first and second curved portions all have substantially the same constant thickness.

12. The prosthetic foot of claim 11 wherein a first cylinder having a radius R1 formed by the continuation of said first curved portion, and a second cylinder having radius R2 formed by the continuation of said second curved portion, are substantially tangent to a plane perpendicular to said first planar surface.

13. In a prosthetic foot having a first planar portion and a second planar portion and a sole portion, wherein said first and second planar portions are connected by a first curved portion having a first predetermined radius of curvature R1, and said second planar portion and said sole portion are connected by a second curved portion having a second predetermined radius of curvature R2, the improvement wherein said first and second planar portions are substantially parallel and the distance between said first and second planar portions is less than twice R1., said first and second curved portions and said sole portion all have substantially the same thickness.

* * * * *